United States Patent [19]

Isakozawa et al.

[11] Patent Number: 4,480,220
[45] Date of Patent: Oct. 30, 1984

[54] ELECTRON ENERGY ANALYZING APPARATUS

[75] Inventors: Shigeto Isakozawa; Morioki Kubozoe, both of Katsuta, Japan

[73] Assignee: Hitachi, Ltd., Tokyo, Japan

[21] Appl. No.: 318,404

[22] Filed: Nov. 5, 1981

[30] Foreign Application Priority Data

Nov. 10, 1980 [JP] Japan ................... 55-157008

[51] Int. Cl.³ .......................................... G01N 27/00
[52] U.S. Cl. .................................. 324/71.3; 250/397
[58] Field of Search ................ 324/71.1, 71.3, 71.4, 324/99 D; 250/397, 311, 305

[56] References Cited

U.S. PATENT DOCUMENTS

| | | | |
|---|---|---|---|
| 3,909,610 | 9/1975 | Kokubo | 250/305 |
| 4,068,123 | 1/1978 | Kokubo | 250/311 |
| 4,109,168 | 8/1978 | Raymond | 324/99 D |

OTHER PUBLICATIONS

*Circuit Design Idea Handbook,* Ed. Bill Furlow, Halliday Lithograph Corp., 1974.

*Primary Examiner*—Michael J. Tokar
*Assistant Examiner*—Kevin D. O'Shea
*Attorney, Agent, or Firm*—Antonelli, Terry & Wands

[57] ABSTRACT

An electron energy analyzing apparatus is disclosed in which electrons having passed through a sample are subjected to energy analysis, respective energy values of the crest and trough of an energy peak characterizing a predetermined substance in the sample are selected, subtraction is performed beetween output signals of a detector obtained respectively at the energy values, the sign of a difference between the output signals is judged to separate a background signal from an energy loss peak signal, and a distribution image of the substance is displayed on the basis of the energy loss peak signal containing no background signal.

12 Claims, 8 Drawing Figures

ELECTRON ENERGY ANALYZING APPARATUS

BACKGROUND OF THE INVENTION

1. Field of the Invention

The present invention relates to an electron energy analyzing apparatus, and more particularly to an apparatus for analyzing the energy of electrons which have passed through a sample.

2. Description of the Prior Art

When an electron beam is incident upon a sample, some of the electrons having passed through the sample do not lose any energy, but the remaining ones lose some energy due to the interaction between the electrons and the sample. Since the energy loss of such electrons depends upon substances making up the sample, it is possible to analyze the constituent substances of the sample on the basis of an energy spectrum of the electrons which have passed through the sample.

When electrons which have passed through a sample are introduced into an electron analyzer, the electrons are dispersed in accordance with their energy. Accordingly, when the energy analyzer is so set as to detect only an energy loss peak caused by a specified substance contained in the sample in order to apply an energy loss peak signal thus obtained to a cathode ray tube as a brilliance modulation signal, and when the sample is two dimensionally scanned by an electron beam and the screen of the cathode ray tube is two-dimensionally scanned by the electron beam of the tube in synchronism with the scanning motion for the sample, an image showing a distribution of the specified substance can be displayed on the screen of the cathode ray tube. This distribution image is usually called the element mapping image.

In the above-mentioned case, however, there arises a problem that the energy loss peak signal which is actually detected, includes a background component which increases with the thickness of the sample.

SUMMARY OF THE INVENTION

An object of the present invention is to provide an electron energy analyzing apparatus which can substantially eliminate the above-mentioned background component.

Another object of the present invention is to provide an electron energy analyzing apparatus which can carry out in a short time the processing for substantially eliminating the background component.

In an electron energy analyzing apparatus according to the present invention, a sample is scanned by an electron beam, electrons which have passed through the sample with the above-mentioned scanning motion, are energy-analyzed, the energy-analyzed electrons are detected to be converted into an electric signal, an energy related to an energy loss peak for characterizing a predetermined substance in the sample is varied in a certain range at a period when the electron beam is directed to a given point on the sample, so that the electric signal includes an energy signal characterizing the substance and a background signal, the energy signal is discriminated from the background signal, and the energy signal thus discriminated is used to display a distribution image of the substance.

These and other objects and features of the present invention will become apparent from the following explanation taken in conjunction with the accompanying drawings.

DESCRIPTION OF THE PREFERRED EMBODIMENT

Figure 1:
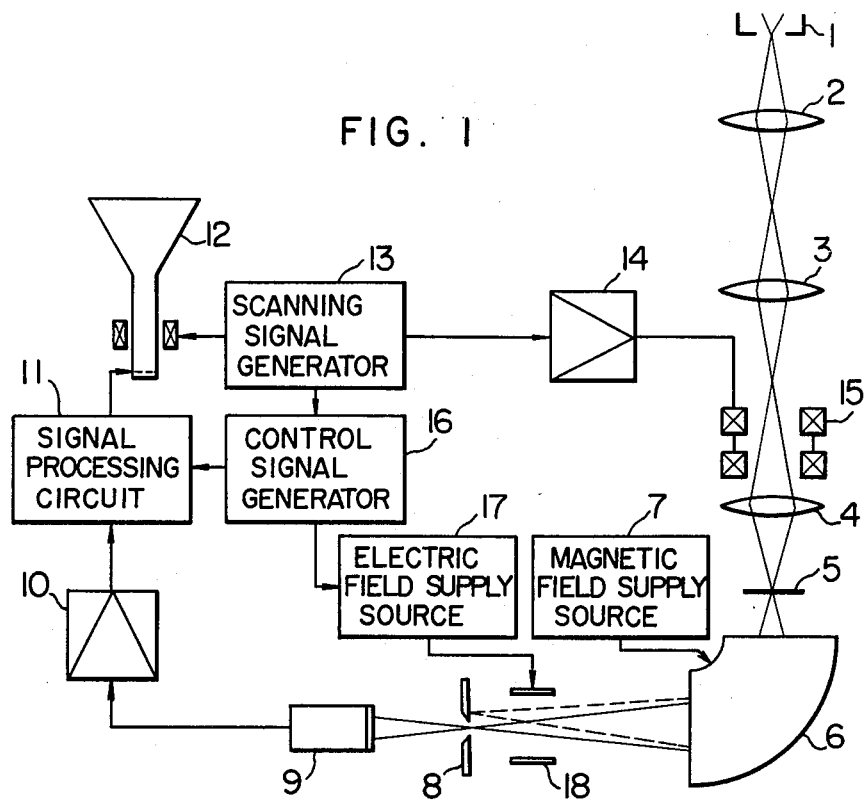
FIG. 1 is a block diagram showing an embodiment of an electron energy analyzing apparatus according to the present invention.

Referring to FIG. 1, an electron beam emitted from an electron gun 1 is focused by condenser lenses 2 and 3, and the focused electron beam is further focused on a sample 5 by an object lens 4. The electron beam focused on the sample 5 passes through the sample 5, and the transmitted electron beam is introduced into an energy analyzer 6. The energy analyzer 6 is an electromagnet forming therein a magnetic field, and the intensity of the magnetic field, that is, the energy of electrons directed to a position can be varied by changing an electric current supplied from a magnetic field supply source 7 to the electromagnet 6.

The electron beam having passed through the sample 5 is dispersed by the energy analyzer 6 in accordance with the energy of the electrons thereof, that is, is divided into a plurality of electron beams. One of these electron beams, which has a specified energy, passes through a slit 8 and is then detected by a detector 9 to be converted into an electric signal. The electric signal is applied as a brilliance modulation signal to a cathode ray tube 12 through an amplifier 10 and a signal processing circuit 11.

X-axis and Y-axis scanning signals generated by a scanning signal generator 13 are applied to a deflecting system of the cathode ray tube 12, and simultaneously are applied to a two-stage deflecting system 15 through an amplifier 14. Thus, the screen of the cathode ray tube 12 is two-dimensionally scanned by the electron beam of the tube 12, and the electron beam incident upon the sample 5 is two-dimensionally deflected in synchronism with the scanning motion in the cathode ray tube 12, that is, the sample 5 is two-dimensionally scanned by the incident electron beam. Accordingly, when only electrons having a specified energy, which characterizes a substance, are drawn out through the slit 8 without performing any energy sweep, a distribution image of the substance, namely, an element mapping image is displayed on the screen of the cathode ray tube 12.

Figure 2:
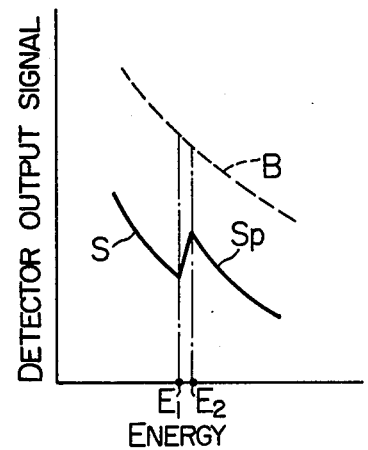
FIG. 2 shows a relation between the energy of electrons which have passed through a sample and the output signal of a detector.

FIG. 2 shows a relation between the energy of electrons which have passed through the sample 5 and the output signal of the detector 9 (namely, the detector output signal). In FIG. 2, reference symbol S designates an energy spectrum, and B a background which increases with the thickness of the sample. Further, a part Sp of the energy spectrum S designates an energy loss peak caused by a substance in the sample 5.

Figure 3:
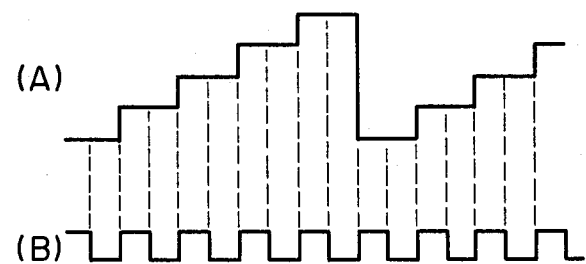
FIG. 3 shows a relation between an X-axis scanning signal generated by the scanning signal generator shown in FIG. 1 and a control signal generated by the control signal generator shown in FIG. 1.

According to the embodiment shown in FIG. 1, an element mapping image in which the background is substantially eliminated, can be displayed. This will be explained below in more detail. The X-axis scanning signal generated by the scanning signal generator 13 has a saw-tooth waveform which varies stepwise as shown in a part (A) of FIG. 3. Accordingly, the scanning motion on the sample 5 in the direction of the X-axis is carried out stepwise. A control signal generator 16 generates such a control signal as shown in another part (B) of FIG. 3. The control signal is synchronized with the abovementioned saw-tooth waveform as shown in FIG. 3, and is used to control an electric field supply source 17. The electric field supply source 17 forms an electric field between a pair of electrodes 18 in such a manner that the electric field is switched over between two values with the same frequency as shown in the part (B) of FIG. 3. The electric field formed between the electrodes 18 is arranged so that electrons moving from the energy analyzer 6 to the slit 8 are deflected perpendicularly to the direction of motion of the electrons. One of the abovementioned values is set so that electrons having an energy $E_1$ which corresponds to a trough of the energy loss peak Sp shown in FIG. 2, can pass through the slit 8, the other value is set so that electrons having another energy $E_2$ which corresponds to the crest of the energy loss peak Sp, can pass through the slit 8. Accordingly, the detector output signals with respect to a point on the sample 5 which correspond respectively to the energy values $E_1$ and $E_2$, are obtained at substantially same time. That is, such substantially simultaneous detector output signals are obtained for the whole scanning region on the sample 5.

Figure 4:
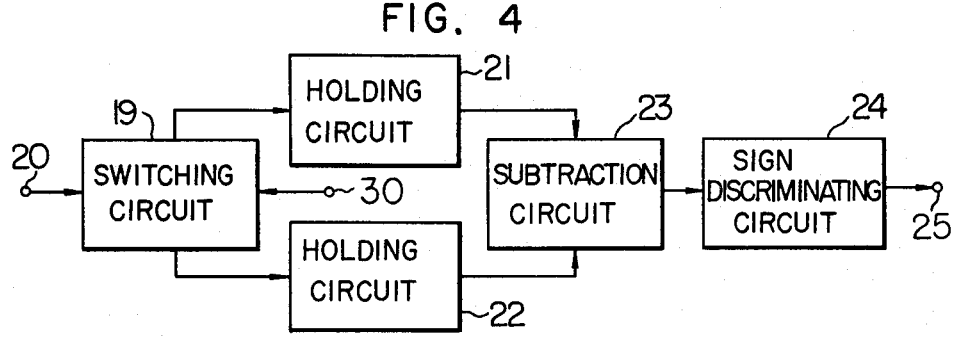
FIG. 4 is a block diagram showing an example of the signal processing circuit shown in FIG. 1.

FIG. 4 shows an example of the signal processing circuit 11 shown in FIG. 1. The control signal which is generated by the control signal generator 16 and shown in the part (B) of FIG. 3, is applied to a switching circuit 19 through a terminal 30, and thereby the detector output signals which are applied from the amplifier 10 to the switching circuit 19 through a terminal 20, are supplied alternately to storing or holding circuits 21 and 22. The outputs of these holding circuits are applied to a comparator, namely, a subtraction circuit 23 to be compared with each other, that is, to perform subtraction between these outputs. As is apparent from FIG. 2, a difference in the detector output signal with respect to the background B between the energy values $E_1$ and $E_2$ and a difference in the detector output signal with respect to the energy loss peak Sp between the energy values $E_1$ and $E_2$ have opposite signs. Accordingly, when the sign of the former is negative, the sign of the latter is positive. Accordingly, the sign of the output from the subtraction circuit 23 is judged by a sign discriminating circuit 24, and the output of the subtraction circuit 23 is applied, as the brilliance modulation signal, from the sign discriminating circuit 24 to the cathode ray tube 12 through a terminal 25 only when the output of the subtraction circuit 23 is positive. Thus, the background B is substantially eliminated from the distribution image of the substance causing the energy loss peak Sp, namely, the element mapping image. This is because the difference in the detector output signal with respect to the background B between the energy values $E_1$ and $E_2$ is, in general, far smaller than the difference in the detector output signal with respect to the energy loss peak Sp between the energy values $E_1$ and $E_2$.

In the embodiment shown in FIG. 1, in order that an electron beam having the energy $E_1$ and another electron beam having the energy $E_2$ pass through the slit 8 alternately, the electrodes 18 for forming an electric field are disposed in front of the slit 8, and the intensity of the electric field is switched over between the two set values. Alternatively, the magnetic field formed by the electromagnet 6 may be controlled so that the intensity of the magnetic field is switched over between two values. However, when a high-speed control, namely, a high-speed switchover is required, the switching of the electric field is preferable due to excellent response.

The background can also be substantially eliminated in a manner that electrons having the energy $E_1$ are detected at the first Y-axis scanning, electrons having the energy $E_2$ are detected at the second Y-axis scanning, and the difference between the detector output signal at the first Y-axis scanning and that at the second Y-axis scanning is used to display the element mapping image. In this case, however, it takes a lot of time to carry out energy analysis. Further, when a time required for the first Y-axis scanning is very long (for example, more than 100 min.), there arises a problem that the sample may suffer a change between the first scanning and the second scanning.

A division circuit may be used as the comparator, in place of the subtraction circuit 23 shown in FIG. 4. In this case, a value obtained by dividing the detector output signal with respect to the background B at the energy position $E_2$ by that at the energy position $E_1$ and a value obtained by dividing the detector output signal with respect to the energy loss peak Sp at the energy position $E_2$ by that at the energy position $E_1$ are compared. As is apparent from FIG. 2, when one of these values is greater than 1, the other value is less than 1. For example, when the above-mentioned value with respect to the background B is less than 1, the value with respect to the energy loss peak Sp is greater than 1. In this case, a circuit which becomes conductive only when the input thereof is greater than 1, is used in place of the sign discriminating circuit 24.

Figure 5:
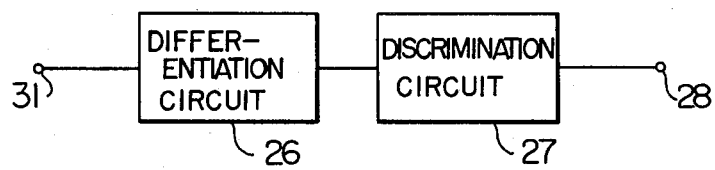
FIG. 5 is a block diagram showing another example of the signal processing circuit shown in FIG. 1.

FIG. 5 shows another example of the signal processing circuit shown in FIG. 1. Referring to FIG. 5, the output of the amplifier 10 is applied to a differentiation circuit 26 through a terminal 31 to be differentiated. It is judged by a discrimination circuit 27 whether the output of the differentiation circuit 26 is positive or not, and the output of the differentiation circuit 26 is applied as the brilliance modulation signal to the cathode ray tube 12 through a terminal 28 only when the above-mentioned output is positive.

Figure 6:
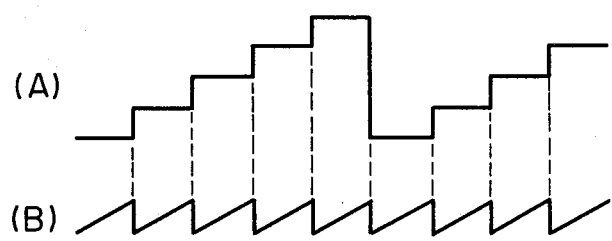
FIG. 6 shows a relation between an X-axis scanning signal and a control signal, which corresponds to but differs from the relation shown in FIG. 3.
Figure 7A:
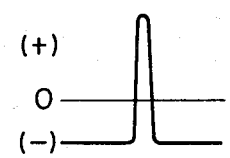
FIGS. 7A and 7B show outputs from the differentiating circuit shown in FIG. 5.
Figure 7B:
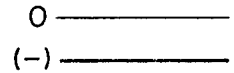

In the case when the signal processing circuit shown in FIG. 5 is used, the X-axis scanning signal has a saw-tooth waveform which varies stepwise as shown in a part (A) of FIG. 6, and the control signal generator 16 generates a control signal which varies continuously at each step of the X-axis scanning signal as shown in a part (B) of FIG. 6. As a result of the use of such a control signal, an energy sweep is carried out between the energy values $E_1$ and $E_2$ shown in FIG. 2. FIGS. 7A and 7B show outputs of the differentiation circuit 26 in the above-mentioned case. That is, FIG. 7A shows a differentiated waveform of the energy loss peak Sp shown in FIG. 2, and FIG. 7B shows a differentiated waveform of the background B shown in FIG. 2. As mentioned previously, the output of the differentiation circuit 26 can pass through the discrimination circuit 27 only when the above-mentioned output is positive. As is apparent from FIG. 7B, the differentiated signal of the background is prevented from being applied to the cathode ray tube 12 through the terminal 28.

Obviously many modifications and variations of the above-mentioned embodiment are possible without departing from the spirit of the invention. It is therefore to be understood that within the scope of the appended claims the invention may be practiced otherwise than as specifically described.

We claim:

1. An electron energy analyzing apparatus comprising:
   means for generating an electron beam;
   means for two-dimensionally scanning a sample with the electron beam;
   means for dispersing electrons transmitted through the sample on scanning the sample with the electron beam in accordance with the energy level of the transmitted electrons;
   means for deflecting the dispersed electrons of different energy levels so that the dispersed electrons of different energy levels are detectable separately when the electron beam scans each scanning position on the sample, said different energy levels including at least a selected energy level related to an energy loss peak characterizing a predetermined substance contained in the sample;
   means for separately detecting the dispersed electrons of different energy levels and for producing output signals corresponding to the dispersed electrons of respectively different energy levels, said output signals including background components;
   means for detecting a specific variation of the output signal corresponding to the dispersed electrons of said selected energy level as compared with the remaining output signals and for producing an electric signal when said specific variation is detected, said specific variation being a variation as detected when the predetermined substance is contained in the sample at the scanning portion thereof; and
   means for displaying a distribution image of the predetermined substance by using the electrical signal for each scanning position on the sample.

2. An energy analyzing apparatus according to claim 1, wherein said background components included in said output signals corresponding to the dispersed electrons of respectively different energy levels vary in accordance with the thickness of the specimen, and said means for detecting said specific variation produces said electric signal with said background components being substantially eliminated.

3. An electron energy analyzing apparatus comprising:
   means for generating an electron beam;
   means for two-dimensionally scanning a sample with the electron beam;
   means for dispersing electrons transmitted through the sample on scanning the sample with the energy level of the transmitted electrons;
   means for deflecting the dispersed electrons of first and second energy levels so that the dispersed electrons of the first and second energy levels are separately detectable when the electron beam scans each scanning position on the sample, said first and second energy levels being related to energy levels of the crest and trough of an energy loss peak characterizing a predetermined substance contained in the sample;
   means for separately detecting the dispersed electrons of the first and second energy levels and for producing first and second output signals corresponding to the dispersed electrons of the first and second energy levels, respectively, said first and second output signals including background components;
   means for comparing one of said first and second output signals with the other of said first and second output signals and for producing an electric signal when a specific variation is detected between said first and second output signals, said specific variation being a variation as detected when the predetermined substance is contained in the sample at the scanning position thereof; and
   means for displaying a distribution image of the predetermined substance by using the electrical signal for each scanning position on the sample.

4. An electron energy enalyzing apparatus according to claim 3, wherein said comparing means comprises means for subtracting one of said first and second output signals from the other of said first and second output signals and for producing said electric signal when the result of the subtraction has a predetermined sign.

5. An electron energy analyzing apparatus according to claim 3, wherein said comparing means comprises means for dividing one of said first and second output signals by the other of said first and second output signals and for producing said electric signal when the result of the division has a value within a predetermined range.

6. An energy analysing apparatus according to claim 3, wherein said background components included in said first and second output signals vary in accordance with the thickness of the sample, and said comparing means produces said electric signal with said background components being substantially eliminated.

7. An electron energy analyzing apparatus comprising:
   means for generating an electron beam;
   means for scanning a sample in directions of X-and Y-axes with the electron beam, said scanning means providing a stepwise scanning in the X-axis direction;
   means for dispersing electrons transmitted through the sample on scanning the sample with the electron beam in accordance with the energy level of the transmitted electrons;
   means for deflecting the dispersed electrons of first and second energy levels so that the dispersed electrons of the first and second energy levels are separately detectable at each step of the electron beam scanning of the sample in the X-axis direction, said first and second energy levels being related to energy levels at the crest and trough of an energy loss peak characterizing a predetermined substance contained in the sample;
   means for separately detecting the dispersed electrons of the first and second energy levels and for producing first and second output signals corresponding to the dispersed electrons of the first and second energy levels, respectively, said first and second output signals including background components;

means for comparing one of said first and second output signals with the other of said first and second output signals and for producing an electric signal when a specific variation is detected between said first and second output signals, said specific variation being a variation as detected when the predetermined substance is contained in the sample at the scanning position thereof; and means for displaying a distribution image of the predetermined substance by using the electrical signal for each scanning position on the sample.

8. An electron energy analyzing apparatus according to claim 7, wherein said comparing means comprises means for subtracting one of said first and second output signals from the other of said first and second output signals and for producing said electric signal when the result of the subtraction has a predetermined sign.

9. An electron energy analyzing apparatus according to claim 7, wherein said comparing means comprises means for dividing one of said first and second output signals by the other of said first and second output signals and for producing said electric signal when the result of the division has a value within a predetermined range.

10. An energy analyzing apparatus according to claim 7, wherein said background components included in said first and second output signals vary in accordance with the thickness of the sample, and said comparing means produces said electric signal with said background components.

11. An electron energy analyzing apparatus comprising:

means for generating an electron beam;

means for two-dimensionally scanning a sample stepwise with the electron beam;

means for dispersing electrons transmitted through the sample on scanning the sample with the electron beam in accordance with the energy level of the transmitted electrons;

means for continuously deflecting the dispersed electrons of different energy levels so that the dispersed electrons of different energy levels are sequentially detectable at each step of the scanning on the sample, said different energy levels including at least a selected energy level related to an energy loss peak characterizing a predetermined substance contained in the sample;

means for sequentially detecting the dispersed electrons of different energy levels and for producing an output signal indicative of a variation of the dispersed electrons of respectively different energy levels, said output signal including a background component;

means for differentiating said output signal and for producing an electric signal when the result of the differentiation indicates a specific variation existing in said output signal, said specific variation being a variation as appearing in said output signal when the predetermined substance is contained in the sample at the scanning position thereof; and means for displaying a distribution image of the predetermined substance by using said electrical signal for each scanning position on the sample.

12. An energy analyzing apparatus according to claim 11, wherein said background component included in said output signal varies in accordance with the thickness of the sample, and said differentiating means produces said electric signal with said background component being substantially eliminated.

* * * * *